(12) United States Patent
Carroll

(10) Patent No.: US 9,320,902 B2
(45) Date of Patent: Apr. 26, 2016

(54) SPINAL CORD STIMULATION WITH INTERFERENTIAL CURRENT

(71) Applicant: Meagan Medical, Inc., Vancouver, WA (US)

(72) Inventor: William J. Carroll, La Center, WA (US)

(73) Assignee: Meagan Medical, Inc., Vancouver, WA (US)

( * ) Notice: Subject to any disclaimer, the term of this patent is extended or adjusted under 35 U.S.C. 154(b) by 0 days.

(21) Appl. No.: 14/606,405

(22) Filed: Jan. 27, 2015

(65) Prior Publication Data

US 2015/0142077 A1 May 21, 2015

Related U.S. Application Data

(62) Division of application No. 10/761,424, filed on Jan. 22, 2004, now Pat. No. 8,977,363.

(60) Provisional application No. 60/441,326, filed on Jan. 22, 2003.

(51) Int. Cl.
*A61N 1/34* (2006.01)
*A61N 1/36* (2006.01)
(Continued)

(52) U.S. Cl.
CPC .......... *A61N 1/36171* (2013.01); *A61N 1/0551* (2013.01); *A61N 1/36071* (2013.01); *A61N 1/36153* (2013.01); *A61N 1/36175* (2013.01); *A61N 1/36185* (2013.01); *A61N 1/36192* (2013.01); *A61N 1/40* (2013.01); *A61N 1/0553* (2013.01)

(58) Field of Classification Search
CPC ........... A61N 1/36171; A61N 1/36185; A61N 1/36071
See application file for complete search history.

(56) References Cited

U.S. PATENT DOCUMENTS 3,096,768 A 7/1963 Griffith, Jr.
3,822,708 A 7/1974 Zilber
(Continued)

OTHER PUBLICATIONS

Kalliomaki, J., Granmo, M., Schouenborg, J., "Spinal NMDA-receptor dependent amplification of nociceptive transmission to rat primary somatosensory cortex (SI)", Pain., Jul. 2003;104(1-2):195-200.
(Continued)

*Primary Examiner* — Michael Kahelin
(74) *Attorney, Agent, or Firm* — McDonnell Boehnen Hulbert & Berghoff LLP

(57) ABSTRACT

A stimulator and a method for the treatment of intractable pain syndromes by electrical stimulation of the spinal cord is disclosed in which implantable electrodes positioned around a targeted area of the spinal cord transmit an interferential current that has a base medium frequency alternating current between 500 Hz-20 KHz. A digital signal processor generates a sine-wave-like waveform from a pulse generator which after further processing is used to generate at least two circuits for use in producing the beat frequency signal. An effective area of stimulation is controlled by the quantity of electrodes, positioning of the electrodes and electrode cross pattern orientation. Amplitude modulation of electrical circuits created at the electrode placements also augments the effective area of stimulation. The stimulator and method reduce accommodation of the body to the electrical stimulation and provide deeper penetration of the resultant signal.

20 Claims, 3 Drawing Sheets

(51) Int. Cl.
*A61N 1/05* (2006.01)
*A61N 1/40* (2006.01)

(56) References Cited

U.S. PATENT DOCUMENTS

| | | | |
|---|---|---|---|
| 4,153,061 | A | 5/1979 | Nemec |
| 4,374,524 | A | 2/1983 | Hudek et al. |
| 4,598,713 | A | 7/1986 | Hansjurgens et al. |
| 4,848,347 | A | 7/1989 | Hall |
| 5,002,053 | A | 3/1991 | Garcia-Rill et al. |
| 5,107,835 | A | 4/1992 | Thomas |
| 5,161,530 | A | 11/1992 | Gamble |
| 5,215,086 | A | 6/1993 | Terry et al. |
| 5,269,304 | A | 12/1993 | Matthews |
| 5,443,486 | A | 8/1995 | Hrdlicka et al. |
| 5,466,247 | A | 11/1995 | Scheiner et al. |
| 5,512,057 | A | 4/1996 | Reiss et al. |
| 5,643,330 | A | 7/1997 | Holsheimer et al. |
| 5,776,173 | A | 7/1998 | Madsen et al. |
| 6,052,624 | A | 4/2000 | Mann |
| 6,233,488 | B1 | 5/2001 | Hess |
| 6,505,078 | B1 | 1/2003 | King et al. |
| 6,871,099 | B1 | 3/2005 | Whitehurst et al. |
| 7,349,743 | B2 | 3/2008 | Tadlock |
| 2001/0031999 | A1 | 10/2001 | Carter et al. |

OTHER PUBLICATIONS

Mediratta and Nicoll, "Conduction velocities of corticospinal axons in the rate studied by recording cortical antidromic responses", J Physiol., Mar. 1983; 336:545-61.

Stewart et al., "Corticospinal responses to electrical stimulation of motor cortex in the rat", Brain Research,Feb. 5, 1990; 508(2):341-4.

Chapman and Yeomans, "Motor cortex and pyramidal tract axons responsible for electrically evoked forelimb flexion: refractory periods and conduction velocities", Neuroscience 1994; 59(3):699-711.

Cheing, et al., "Analgesic effects of transcutaneous electrical nerve stimulation and interferential currents on heat pain in healthy subjects", J. Rehabil Med., 2003; 35:15-19.

De Domenico, "Technical aspects of interferential currents", New dimensions in interferential therapy a theoretical & clinical guide, Apr. 1987; chapter 2, 12-16.

Kamondetdacha et al., "Calculations of induced current distribution in a human model from low frequency electrodes" School of Electrical and Computer Engineering, Purdue University, Jul. 26, 2005; 1-33.

Holsheimer et al., "Effectiveness of spinal cord stimulation in the management of chronic pain: analysis of technical drawbacks and solutions", Neurosurgery: vol. 40(5) May 1997; 990-99.

K. Kumar et aL, "Spinal Cord Stimulation versus Conventional Medical Management for Neuropathic Pain: A Multicentre Randomised Controlled Trial in Pateients with Failed Back Surqerv Syndrome" PAIN 132 (2007) 197-188.

M.L Carter, "Spinal Cord Stimulation in Chronic Pain: A Review of Evidence" Anaesth Intensive Care (2004), vol. 32, No. 1, pp. 11-21.

R.S. Taylor et aL, "Spinal Cord Stimulation for Chronic Back and Leg Pain and Failed Back Surgery Syndrome: A Systematic Review and Analysis of Prognostic Factors", (2004), Spine, col. 30, No. 1, pp. 152-160.

R.B. North, et al., "Spinal Cord Stimulation for Chronic Pain of Spinal Origin", (2002), Spine, col. 27, No. 22, pp. 2584-2591.

B. Donner et al., "Long-Term Effects of Nerve Blocks in Chronic Pain", (Oct. 1998), Current Opinion in Anaesthesiology, vol. 11, No. 5, pp. 523-532.

H.P. Vogel et al., "Long-term Effects of Spinal Cord Stimulation in Chronic Pain Syndromes", 1(1986), Journal of Neurology, vol. 233, pp. 16-18.

Barolat, G. et al., "Multifactorial Analysis of Epidural Spinal Cord Stimulation", (1991), Sterotact Funct Neurosurg, No. 56:, pp. 77-103.

"Which Neuronal Elements are Activated Directly by Spinal Cord Stimulation," J. Holsheimer, Institute for Biomedical Technology, University of Twente, pp. 25-31 (2002).

SPINAL CORD STIMULATION WITH INTERFERENTIAL CURRENT

REFERENCE TO RELATED APPLICATION

The present application claims priority to U.S. patent application Ser. No. 10/761,424 filed on Jan. 22, 2004, which claims the benefit of U.S. Provisional Patent Application No. 60/441,326 filed Jan. 22, 2003, both of which are hereby incorporated by reference in their entirety into the present disclosure.

Field of the Invention

The present invention is generally related to spinal cord stimulation and, more particularly, is related to an apparatus and method for the electrical stimulation of the spinal cord using an interferential current pattern for treating chronic pain conditions.

BACKGROUND OF THE INVENTION

Electrical stimulation of the posterior spinal cord, spinal cord stimulation (SCS), has developed into an effective therapeutic tool for treating chronic pain conditions. However, very little is known about the sites of activation or the neural mechanisms evoked by SCS that relieve pain and promote changes in the function of somatic and visceral structures.

Spinal Cord Stimulation is most commonly used for patients with chronic intractable pain syndromes. It has also been useful for treating movement disorders and is occasionally used following head injuries. However, one complication with SCS is that of accommodation or habituation to the stimulation signal. Companies that manufacture spinal stimulation devices have developed complex stimulation programs and devoted chapters on techniques to reduce the problem of accommodation during SCS (Alfano S, Darwin J, Picullel B: Spinal Cord Stimulation, Patient Management Guidelines for Clinicians, Medtronic, Inc.). Accommodation is when the body habituates or becomes accustomed to an activity or signal and then starts to ignore or 'tune it out'. By varying the signal or keeping the focal point of the signal moving, accommodation can be minimized. The concept of using interferential stimulation with implantable leads to decrease the problem of accommodation might prove to be advantageous.

Dorsal Column Stimulation (DCS) or SCS using an electrical interferential current pattern has shown to be a cost benefit in treating chronic pain disorders in patients (Dorsal column stimulation: cost to benefit analysis; Acta Neurochir Suppl (Wien), 52( ): 121-3, 1991).

SCS stimulates the dorsal column in a somewhat superficial manner as pointed out by Holsheimer (Holsheimer J: Which Neuronal Elements are activated Directly by Spinal Cord Stimulation, *Neuromodulation*, Volume 5, Number 1: 25-31, 2002). The electrodes are normally attached to the dura matter in the epidural space, and most of the current distribution remains in the cerebrospinal fluid (CSF) and does not project deeply into the dorsal column. Providing an interferential component to the electrode array of the SCS allows the crossing of the two signals wherein the resultant additive effect of the beat frequency produces deeper penetration of the signal and a higher resultant amplitude at the stimulation site. The interferential current would recruit larger numbers of dorsal column fibers and provide greater levels of pain relief and benefit to intractable pain patients.

Thus, a heretofore unaddressed need exists in the industry to address the aforementioned deficiencies and inadequacies with regard to accommodation or habituation to the spinal cord stimulation signal when used in the treatment of chronic pain syndromes.

SUMMARY OF THE INVENTION

Embodiments of the present invention provide an apparatus and method for the treatment of chronic pain syndromes using electrical stimulation of the spinal cord. The present invention utilizes an interferential current that has a base medium frequency alternating current between 500 Hz and 20 KHz. An interferential current is set up between two circuits that are arranged in a cross-pattern on the subject's targeted area of stimulation. Where the circuits superimpose in a cross-pattern, the resultant beat frequency will be the difference between the frequencies of the two circuits and the amplitude will be additive and greater than either circuit alone. The range of the beat frequency is usually between 1-250 Hz. Multiple levels of stimulation can be treated depending upon the electrode placement, pairing and modulation pattern selected. The range of output would be from 0-11 volts per circuit depending on the patient's needs and the pulse width is commonly set at 210 microseconds but it could range from 10-600 microseconds. The amplitude can be modulated in the respective circuits to increase the area of targeted stimulation. This type of current (Interferential) provides improved directional control, decreased accommodation/habituation and increased depth of penetration in comparison to other standard implantable stimulation systems and their accompanying surgical leads. The amplitudes of the outputs in the respective circuits may be modulated to increase the area of targeted stimulation. Interferential current allows improved directional control and depth of penetration in comparison to other stimulation techniques.

Briefly described, in architecture, one embodiment of the invention, among others, can be implemented as follows.

Digital signal processors (DSPs) are used for improving the accuracy and reliability of digital signals that are used extensively in the communications field. Digital signal processing works by standardizing or clarifying the output of a digital signal. In this embodiment, the digital signal processor is used to shape multiple pulsatile waveforms to approximate the output of a sine-wave generator. In another embodiment of the invention, the digital signal processor is replaced with a field-programmable gate array (FPGA). An FPGA is an integrated circuit that can be programmed in the field after it is manufactured and therefore allows users to adjust the circuit output as the needs change. Both the DSP and the FPGA process a digital signal into a pseudo-sine-wave current waveform from the digital pulses generated by a pulse generator. The pseudo-sine-wave current waveform is transmitted through implantable quadripolar leads with eight electrodes at a targeted area creating a pair of interferential currents.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

A preferred embodiment of the invention and modifications thereof will now be described with reference to the drawings.

Figure 1:
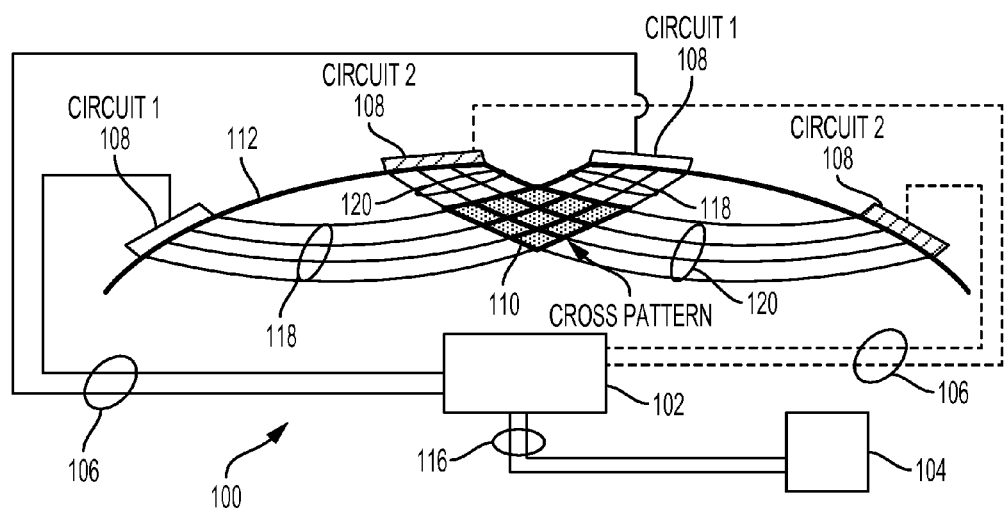
FIG. 1 is a perspective view of an interferential current set up by two circuits that are arranged in a cross pattern.

FIG. 1 shows a stimulator 100 for the electrical stimulation of the spinal cord utilizing an interferential current 110 that has a base medium frequency alternating current within the range of 500 Hz-20 KHz. The interferential current 110 is set up between two circuits 118, 120 that are arranged in a cross-pattern. A first pair of implantable electrodes 108, 208 are positioned on a subject's spinal column 112, preferably the dorsal column, at one set of diagonal corners of a targeted area 214 (see FIG. 2). A second pair of implantable electrodes 108, 208 is then positioned at the other set of diagonal corners of the targeted area 214. Preferably, the electrodes 108 are attached to the dura matter in the epidural space. A digital signal processor 102 is connected to the first and second pairs of surface electrodes 108. When a signal generating source 104 is connected to the digital signal processor 102, a sine-wave-like waveform signal output 106 is created. The digital signal processor 102 improves the accuracy and reliability of digital signals. The digital signal processor 102 processes the multiple pulses 116 from the signal generating source 104 to approximate a sine-wave (pseudo-sine-wave or sine-wave-like). Thus, that type of current recruits larger numbers of dorsal column fibers and provides greater levels of pain relief.

Figure 2:
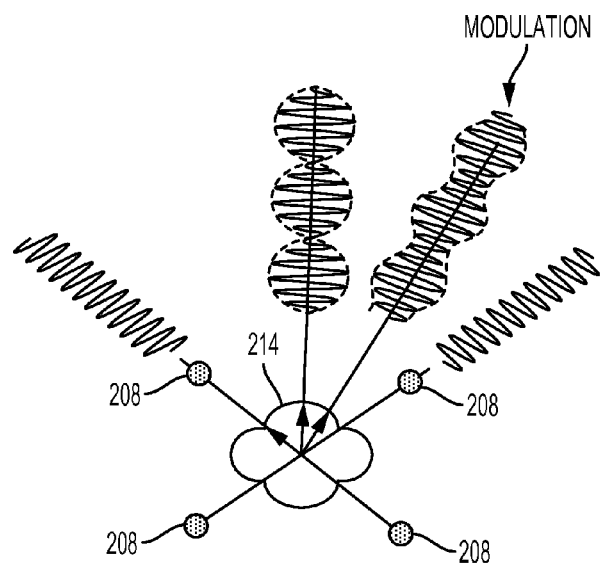
FIG. 2 is a perspective view of an interferential current pattern indicating the current intensity level and area of beat frequency formation.

The digital signal processor 102 generates individual pulses 106 of differing widths and resultant amplitudes. Preferably, the pulse width is set at 210 microseconds, but can range from 50-600 microseconds. When those differing pulses 106 are driven into a transformer (not shown), the pseudo-sine-wave is produced. A pulse generator 104 is connected to the digital signal processor 102 and supplies a pulsed digital signal output 116 to the digital signal processor 102. The digital signal 106 processed by the digital signal processor 102 creates a first circuit 118 and a second circuit 120 at the first and second pairs of surface electrodes 108, 208, respectively. Preferably, the range of output of the electrical circuits 118, 120 are 0-11 volts per circuit, depending on the patient's needs for pain treatment. Where the first and second circuits 118, 120 superimpose (cross), the resultant beat frequency (which is preferably between 1 and 250 beats/second) will be the difference between the frequencies of the two circuits, and the amplitude will be additive and greater than either circuit alone (FIG. 2).

Figure 3:
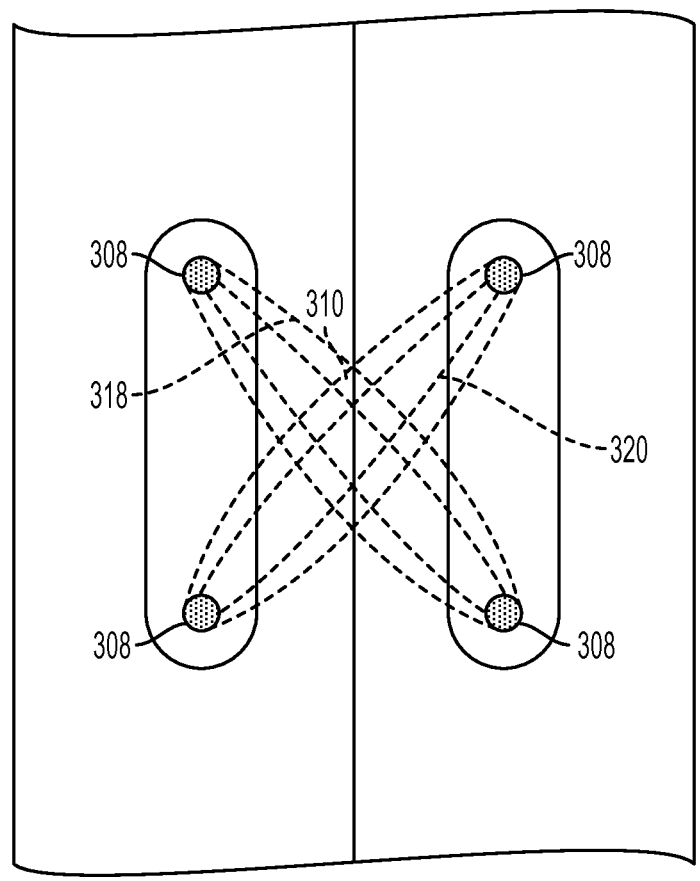
FIG. 3 is a perspective view illustrating the effective area of stimulation resulting from the crossing of separate circuits.

Multiple target areas of the spinal cord can be treated depending upon the quantity and placement of the first and second pairs of electrodes 308, and by modulating the amplitudes of the outputs of the first and second circuits 318, 320 (see FIG. 3). Modulating the outputs of the first and second circuits 318, 320 increases the area of the targeted stimulation. The depth of modulation can vary from 0 to 100% and depends on the direction of the currents established by the first and second circuits 318, 320. It has been shown that when the first and second circuits 318, 320 intersect at 90°, the maximum resultant amplitude and the deepest level of modulation is half-way between the two circuits (45° diagonally). (See FIG. 2). Hence, the target area of stimulation can be augmented by modulation of the amplitudes of the outputs of the two circuits.

Figure 4:
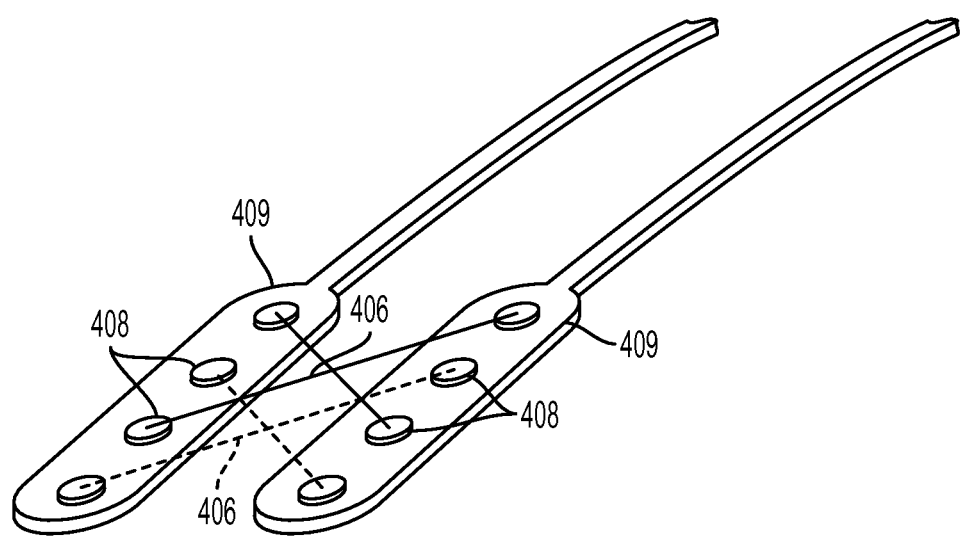
FIG. 4 is a diagram illustrating interferential stimulation using two implantable quadripolar leads.

FIG. 4 illustrates two interferential currents 406 with sine-wave-like waveforms that are produced by two implantable quadripolar leads 409. Each quadripolar lead 40 includes four electrodes 408 for a total of eight. The two quadripolar leads 409 allow a greater target treatment stimulation area of the spinal cord. However, the invention could also apply to the use of two bipolar or octapolar lead systems, and other suitable devices. The electrodes could be activated in various combinations and patterns, and not just as shown in the drawings.

A field-programmable gate array (not shown) can also be used to shape multiple pulsatile waveforms to approximate the output of a sine-wave generator instead of the digital signal processor 102 described above. The FPGA is an integrated circuit that can be programmed in the field after it is manufactured and allows its user to adjust the circuit output as desired. In an alternative embodiment, the digital signal processor may be replaced with the FPGA. Whereas DSP processors typically have only eight dedicated multipliers at their disposal, a higher end FPGA device can offer up to 224 dedicated multipliers plus additional logic element-based multipliers as needed. That allows for complex digital signal processing applications such as finite impulse response filters, forward error correction, modulation-demodulation, encryption and applications such as utilized in the present invention.

It should be emphasized that the above-described embodiments of the present invention, particularly, any "preferred" embodiments, are merely possible examples of implementations, merely set forth for a clear understanding on the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

I claim:

1. A method for the treatment of chronic pain syndromes using electrical stimulation of the spinal cord, the method comprising:

positioning a first pair of implantable electrodes to a dura matter in an epidural space proximate to a subject's spinal cord at predetermined locations;

positioning a second pair of implantable electrodes to the dura matter in the epidural space proximate to the subject's spinal cord at predetermined locations; and transmitting signals of first and second frequencies through the first and second pairs of implantable electrodes respectively, so that the signals of the first and second frequencies interfere with each other to produce at least one beat signal proximate to the subject's spinal cord using a current with a base medium frequency of at least 500 Hz but no more than 20 KHz, and wherein a majority of the at least one beat signal is directionally distributed and controlled, enabling the at least one beat signal to avoid remaining in and shunting through cerebrospinal fluid proximate to the subject's spinal cord, thereby recruiting dorsal column fibers.

2. The method of claim 1, further comprising positioning the first pair of implantable electrodes and the second pair of implantable electrodes so that a first circuit is created between a first electrode of the first pair of implantable electrodes and a first electrode of the second pair of implantable electrodes and so that a second circuit is created between a second electrode of the first pair of implantable electrodes and a second electrode of the second pair of implantable electrodes, wherein the first circuit and the second circuit are arranged to cross one another.

3. The method of claim 2, wherein the first circuit and the second circuit interfere to create a resultant signal having a resultant beat frequency that is a difference between the first and second frequencies and an amplitude that is additive and more than an amplitude of the signal of the first frequency.

4. The method of claim 3, wherein the first and second circuits cross at about 90° resulting in a maximum amplitude of the resultant signal.

5. The method of claim 3, wherein the first and second circuits cross at about 90° and a resulting modulation of the resultant signal is a deepest level of modulation at about 45° between the first and second circuits.

6. The method of claim 3, wherein the first and second circuits cross and a resulting modulation of the resultant signal varies in intensity between the first and second circuits.

7. The method of claim 1, further comprising altering a targeted area of the subject's spinal cord by modulating amplitudes of the signals of first and second frequencies.

8. The method of claim 1, further comprising:
supplying digital signal pulses to a digital signal processor via a pulse generator;
the digital signal processor processing the digital signal pulses to approximate a sine-wave-like output waveform; and
transmitting the sine-wave-like output waveform as signals of the first and second frequencies through the first and second pairs of implantable electrodes.

9. The method of claim 1, further comprising varying locations of the first and second pairs of implantable electrodes along the spinal cord.

10. The method of claim 1, further comprising modulating amplitudes of outputs of the first and second pairs of implantable electrodes.

11. The method of claim 1, wherein the method includes using the current with a resultant beat frequency of no more than 250 Hz.

12. The method of claim 1, wherein the method includes using the current with a voltage output of 11 volts maximum.

13. The method of claim 1, wherein the method includes using the current with a pulse width of 210 microseconds.

14. The method of claim 1, wherein the method includes using the current with a pulse width comprising a range of at least 10 microseconds but no more than 600 microseconds.

15. The method of claim 1, wherein the first pair of implantable electrodes and the second pair of implantable electrodes are included on two quadripolar leads.

16. A method for treatment of chronic pain syndromes using electrical stimulation of the spinal cord, the method comprising:
positioning a first implantable lead to a dura matter in an epidural space proximate to a subject's spinal cord at predetermined locations proximate to a targeted area, the first implantable lead including at least four electrodes;
positioning a second implantable lead to a dura matter in an epidural space proximate to a subject's spinal cord at predetermined locations proximate to a targeted area, the second implantable lead including at least four electrodes; and
transmitting signals of first and second frequencies through the first implantable lead and the second implantable lead so that the signals of the first and second frequencies interfere to create at least one beat signal proximate to the targeted area using a current with a base medium frequency of at least 500 Hz but no more than 20 KHz, and wherein a majority of the at least one beat signal is directionally distributed and controlled, enabling the at least one beat signal to avoid remaining in and shunting through cerebrospinal fluid proximate to the subject's spinal cord, thereby recruiting dorsal column fibers.

17. The method of claim 16, further comprising positioning the first implantable lead and the second implantable lead so that (i) a first circuit is created between a first electrode of the at least four electrodes of the first implantable lead and a first electrode of the at least four electrodes of the second implantable lead, and (ii) a second circuit is created between a second electrode of the at least four electrodes of the first implantable lead and a second electrode of the at least four electrodes of the second implantable lead, wherein the first circuit and the second circuit are arranged to cross one another.

18. The method of claim 17, wherein at a crossing point of the first circuit and the second circuit, the signals of the first and second frequencies interfere to create the at least one beat signal.

19. The method of claim 16, further comprising positioning the first implantable lead and the second implantable lead so that (i) a third circuit is created between a third electrode of the at least four electrodes of the first implantable lead and a third electrode of the at least four electrodes of the second implantable lead, and (ii) a fourth circuit is created between a fourth electrode of the at least four electrodes of the first implantable lead and a fourth electrode of the at least four electrodes of the second implantable lead, wherein the third circuit and the fourth circuit are arranged to cross one another.

20. The method of claim 19, further comprising: connecting a pulse generator to a digital signal processor and supplying digital signal pulses to a field-programmable gate array which produces a sine-wave-like current waveform which is further processed and output to the first implantable lead and the second implantable lead.

\* \* \* \* \*